US012682122B2

(12) United States Patent
Marlborough et al.

(10) Patent No.: US 12,682,122 B2
(45) Date of Patent: Jul. 14, 2026

(54) SYSTEMS AND METHODS FOR QUARANTINE PRESERVATION OF DATA INTEGRITY IN DATA MANAGEMENT SYSTEMS

(71) Applicant: Veeva Systems Inc., Pleasanton, CA (US)

(72) Inventors: Michelle Louise Marlborough, Red Hook, NY (US); Bonnie Bates, Kansas City, MO (US)

(73) Assignee: Veeva Systems Inc., Pleasanton, CA (US)

( * ) Notice: Subject to any disclaimer, the term of this patent is extended or adjusted under 35 U.S.C. 154(b) by 0 days.

(21) Appl. No.: 19/412,809

(22) Filed: Dec. 8, 2025

(65) Prior Publication Data

US 2026/0161828 A1 Jun. 11, 2026

Related U.S. Application Data

(60) Provisional application No. 63/729,194, filed on Dec. 6, 2024.

(51) Int. Cl.
*G06F 21/64* (2013.01)
*G16H 10/60* (2018.01)

(52) U.S. Cl.
CPC ............. *G06F 21/64* (2013.01); *G16H 10/60* (2018.01)

(58) Field of Classification Search
CPC ................................ G06F 21/64; G16H 10/60
See application file for complete search history.

(56) References Cited

U.S. PATENT DOCUMENTS

| | | | | |
|---|---|---|---|---|
| 8,407,240 B2 * | 3/2013 | Denton | ............... | H04L 63/1433 |
| | | | | 707/766 |
| 2005/0267954 A1 * | 12/2005 | Lewis | ................. | H04L 63/0823 |
| | | | | 709/221 |
| 2007/0030539 A1 * | 2/2007 | Nath | ..................... | H04W 12/08 |
| | | | | 358/520 |
| 2009/0099867 A1 * | 4/2009 | Newman | ................ | G16H 40/20 |
| | | | | 705/2 |
| 2021/0295956 A1 * | 9/2021 | Adhikari | ............. | G06F 16/1873 |
| 2023/0233388 A1 * | 7/2023 | Bodurka | ................ | A61G 7/018 |
| | | | | 700/275 |
| 2025/0266175 A1 * | 8/2025 | Achara | .................. | G16H 10/20 |

* cited by examiner

*Primary Examiner* — Hany S. Gadalla

(57) ABSTRACT

A computer-implemented method for quarantine preservation of outcome assessment data integrity in data management systems. The data management system receives an outcome assessment successfully completing a first set of client-side validations, wherein the first set of client-side validations include a series of validations checking for required fields and format checks. A second set of server-side validations is executed including a series of validations checking for uniqueness constraints, complex business rules, cross-referencing with other database records, and consistency. When one server-side validation in the second set of server-side validations fails, the outcome assessment successfully completing the first set of client side validations in a quarantine repository is stored and updated to quarantined state. The outcome assessment is modified to correct the failed server-side validation and subsequently validated a second time.

11 Claims, 7 Drawing Sheets

300

120a

SYSTEMS AND METHODS FOR QUARANTINE PRESERVATION OF DATA INTEGRITY IN DATA MANAGEMENT SYSTEMS

CROSS REFERENCE TO RELATED APPLICATIONS

This application claims priority to U.S. Provisional Patent Application No. 63/729,194, filed on Dec. 6, 2024, which is incorporated herein by reference in its entirety.

TECHNICAL FIELD

The present disclosure relates generally to systems and methods for data management, including platforms and approaches that provide for quarantine preservation of data integrity in data management systems.

BACKGROUND

There is a critical deficiency in data management systems, particularly those utilizing mobile or client-side applications for data capture submission. The core issue lies in the discrepancy between successful client-side validation and subsequent backend validation failure, leading to data loss risk despite the user's perception of successful submission.

SUMMARY OF THE INVENTION

Embodiments disclosed in the present document provide systems and methods for quarantine preservation of outcome assessment data integrity in data management systems. The computer-implemented method comprises: receiving, by the data management system, an outcome assessment successfully completing a first set of client-side validations, wherein the first set of client-side validations include a series of validations checking for required fields and format checks; executing, by the data management system, a second set of server-side validations including a series of validations checking for uniqueness constraints, complex business rules, cross-referencing with other database records, and consistency; when one server-side validation in the second set of server-side validations fails, storing the outcome assessment successfully completing the first set of client side validations in a quarantine repository; updating the outcome assessment status to quarantined state; modifying, by the data management system, the outcome assessment to correct the failed server-side validation; subsequently executing, by the data management system, the second set of server-side validations a second time; and when the second set of server-side validations competes with no errors, updating the outcome assessment status and storing the modified outcome assessment.

BRIEF DESCRIPTION OF THE DRAWINGS

For a more complete understanding of the present application and its advantages, references are now made to the following description taken in conjunction with the accompanying drawings, in which like reference numbers indicate like features.

Although similar reference numbers may be used to refer to similar elements for convenience, it can be appreciated that each of the various example embodiments may be considered to be distinct variations.

Figure 1A:
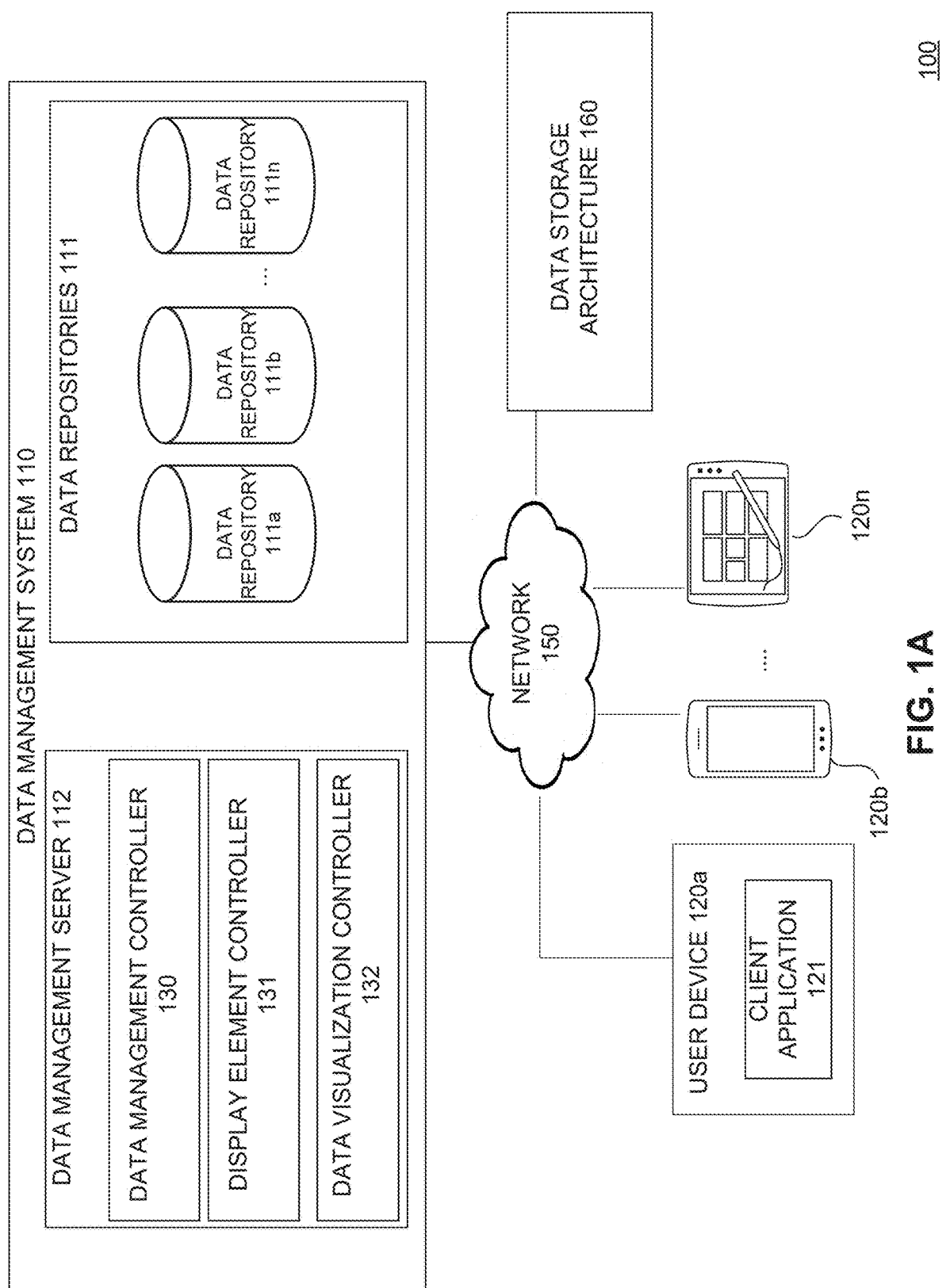
FIG. 1A illustrates an example high level block diagram of a database system architecture wherein the present invention may be implemented.

The present embodiments will now be described hereinafter with reference to the accompanying drawings, which form a part hereof, and which illustrate example embodiments which may be practiced. As used in the disclosures and the appended claims, the terms "embodiment" and "example embodiment" do not necessarily refer to a single embodiment, although it may, and various example embodiments may be readily combined and interchanged, without departing from the scope or spirit of the present embodiments. Furthermore, the terminology as used herein is for the purpose of describing example embodiments only, and are not intended to be limitations. In this respect, as used herein, the term "in" may include "in" and "on," and the terms "a", "an", and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated list items.

DETAILED DESCRIPTION OF INVENTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, well-known structures and components are shown in block diagram form in order to avoid obscuring the concepts of the subject technology.

The current disclosure provides a technical solution for a technical problem in the field of data management systems, particularly those utilizing mobile or client-side applications. When a user submits data from a client device (e.g., mobile application), the data typically undergoes two layers of validation. First, there is a client-side validation, wherein checks are performed before transmission (e.g., checking for required fields, format checks). A user sees the data as submitted upon completion of the client-side validation. Subsequent to a successful client-side validation, there is also a backend validation which contains more rigorous and comprehensive checks performed on the server (e.g., uniqueness constraints, complex business rules, cross-referencing with other database records, consistency checks, etc.). The technical challenge arises when the data passes the client check but fails the backend check. Current systems often handle this by repeatedly attempting to resubmit the data from the client, or simply discarding it. If the client application is closed, uninstalled, or its data is cleared before the issue is resolved, the seemingly submitted data is permanently lost. The technical solution involves an intermediary quarantine and recovery mechanism at the server level to explicitly handle data that fails rigorous backend validation.

FIG. 1A illustrates an example high level block diagram of a database management system architecture 100 wherein the present invention may be implemented. As shown, the architecture 100 may include a data management system 110, a plurality of user computing devices 120a, 120b, . . . 120n, and a data storage architecture 160 coupled to each other via a network 150. The data management system 110 may include data repositories 111 and a data management server 112. The data repositories 111 may have two or more data repositories, e.g., 111a, 111b, . . . and 111n. The network 150 may include one or more types of communication networks, e.g., a local area network ("LAN"), a wide area network ("WAN"), an intra-network, an inter-network (e.g., the Internet), a telecommunication network, and peer-to-peer networks (e.g., ad hoc peer-to-peer networks), which may be wired or wireless.

The user computing devices 120a-120n may be any machine or system that is used by a user to access the content management system 110 via the network 150, and may be any commercially available computing devices including laptop computers, desktop computers, mobile phones, smart phones, tablet computers, netbooks, and personal digital assistants (PDAs). A client application 121 may run from a user computing device, e.g., 120a, and access data in the database management system 110 via the network 150. User computing devices 120a-120n are illustrated in more detail in FIG. 4.

The data repositories 111 may store data that client applications (e.g., 121) in user computing devices 120a-120n may access and may be any commercially available storage devices.

The data management server 112 is typically a remote computer system accessible over a remote or local network, such as the network 150. The data management server 112 could be any commercially available computing devices. A client application (e.g., 121) process may be active on one or more user computing devices 120a-120n. The corresponding server process may be active on the data management server 112. The client application process and the corresponding server process may communicate with each other over the network 150, thus providing distributed functionality and allowing multiple client applications to take advantage of the information-gathering capabilities of the content management system 110.

The data management system 100 may have a data management controller 130 for data duplication management, display element controller 131, and data visualization controller 132.

The data storage architecture 160 may be, e.g., a data warehouse, and may be operated by a third party.

In one implementation, the data management system 110 may be a multi-tenant system where various elements of hardware and software may be shared by one or more customers. For instance, a server may simultaneously process requests from a plurality of customers, and the data repositories 111 may store data for a plurality of customers. In a multi-tenant system, a user is typically associated with a particular customer. In one example, a user could be an employee of one of a number of pharmaceutical companies which are tenants, or customers, of the data management system 110.

In one embodiment, the data management system 110 may run on a cloud computing platform. Users can access content on the cloud independently by using a virtual machine image, or purchasing access to a service maintained by a cloud database provider.

In one embodiment, the data management system 110 may be provided as Software as a Service ("SaaS") to allow users to access the content management system 110 with a thin client.

The present invention allows users to configure what to display on a custom report and how to arrange and display the content (e.g., size, color, theme, form, duration) on the custom report, so that they can visualize the data the way they want. A data visualization interface may be used to generate the custom report, and may have code in a markup language for describing and defining the content of the custom report. One example of the markup language is HyperText Markup Language ("HTML"), and the HTML code may specify the data to be displayed and their location on the custom report according to user configuration. The data visualization interface may also have code in a programming language for describing the custom report's functionality, which may be, e.g., JavaScript code for specifying the objects and fields users want to query to obtain the data to fill up the custom report. The data is returned to the data visualization interface in JSON format. The JavaScript code may place the data, additional data insight, or custom display element at the right place on the custom report, using the HTML to display the custom report.

Users may modify the objects and fields they like to query using the data visualization interface. The data visualization controller 132 modifies the JavaScript accordingly. The data visualization interface could be a webpage, iFrame, or Webview. The data visualization controller 132 may also manipulate the objects and fields by performing calculations to generate a new data element. Various data elements may be selected and translated into a display element in the custom report. The data visualization interface may also have code in a programming language for describing the form of the display element.

The present invention provides an application programming interface ("API") which may communicate with the JavaScript in the data visualization interface and then query data and objects in the data storage architecture 160, data repository 111a, . . . , or data repository 111n to get a result set.

In one implementation, the user may select methods to use from the data access library to interact with the API.

When there is a child application, one application that lives within another installed application, the child application usually communicates through the API provided by the parent application to a data source inside the parent application or external to and exposed through the parent application. Should this child application live within multiple parent applications that provide potentially distinct APIs, the child application would contain multiple pathways through the logic in the application to accommodate these differences in the parent application APIs.

The data visualization of the present invention may facilitate the creation of custom content for data from various platforms. The data visualization controller 132 of the present invention may be integrated as a portion of the various platform web applications, and live as a child application within these parent applications. In order to make convenient use of the data, or data from one or more external data storages, whether it is available through network calls or locally within the parent application, the data access library may expose an API for interacting with the data.

In one implementation, the API may be a unified API which may query various types of data sources across multiple platforms, e.g., iOS, Windows, and the browser for Salesforce online. What a user frequently queries (e.g., the last five calls, most recent calls or all calls submitted) may be packaged up in well formed API calls. The JavaScript may communicate with the API only, and does not have to care about the type of the actual database to be queried. Multiple APIs from multiple providers, utilizing different API styles (e.g., REST, GraphQL, SOAP, RPC, etc.), may send payloads in various data formats (JSON, XLM, etc.) and use different data models. Meeting each providers integration requirements can be made in order to facilitate reliable connections with multiple providers.

Figure 1B:
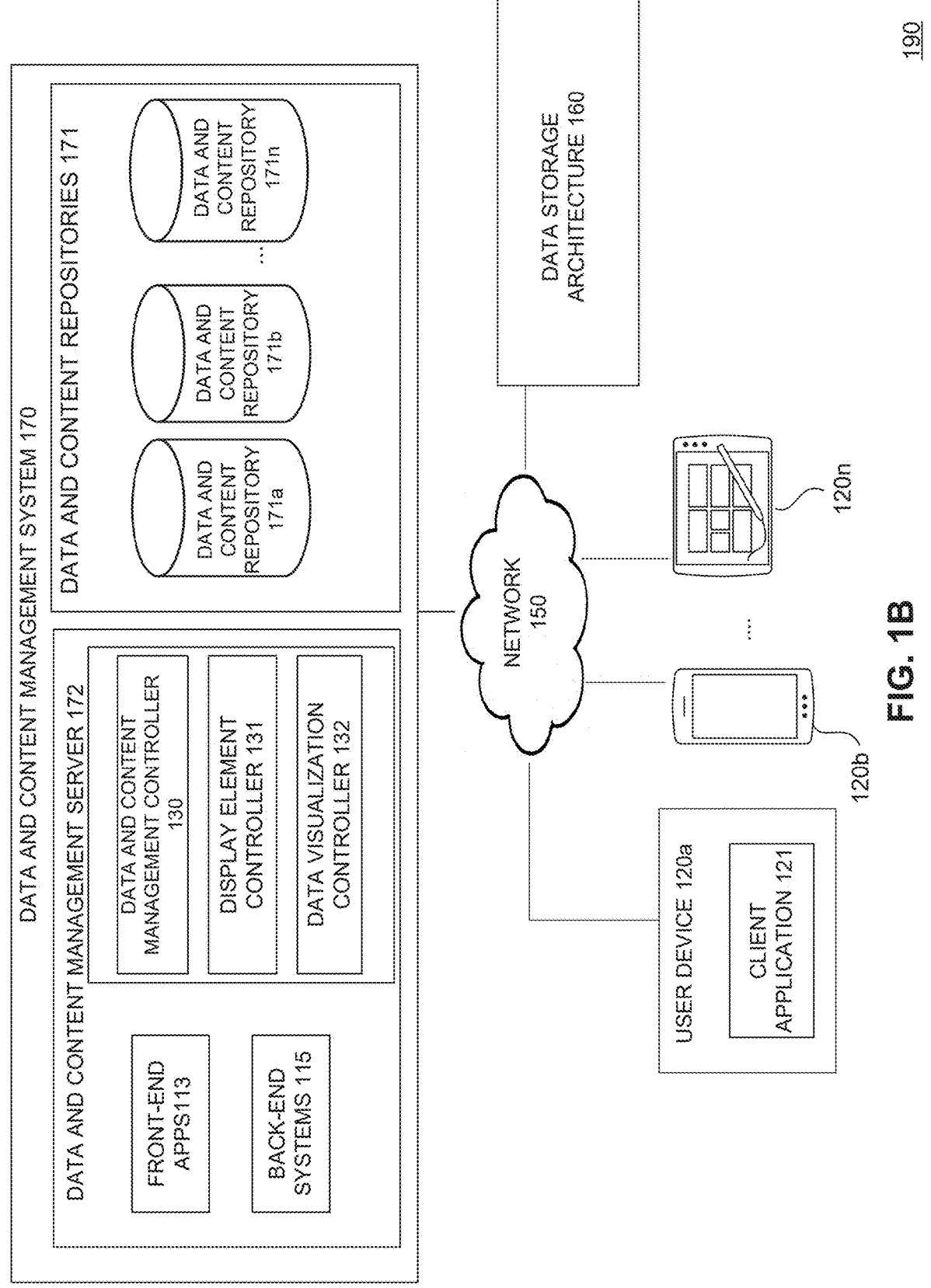
FIG. 1B illustrates an example high level block diagram of an enterprise content management architecture wherein the present invention may be implemented.

FIG. 1B illustrates an example high level block diagram of an enterprise data and content management architecture 190 wherein the present invention may be implemented. The enterprise may be a business, or an organization. As shown, the architecture 190 may include a data and content management system 170, a plurality of user computing devices 120a, 120b, . . . 120n, and a data storage architecture 160 coupled to each other via a network 150. The data and content management system 170 may include a data and content repositories 171 and a data and content management server 172. The data and content repositories 171 may have two or more data and content repositories, e.g., 171a, 171b, . . . and 171n.

The data and content repositories 171 may store data and content that client applications (e.g., 121) in user computing devices 120a-120n may access and may be any commercially available storage devices. As will be described with reference to FIG. 2 below, each data and content repository (e.g., 171a, 171b or 171n) may store a specific category of content, be the source repository for its content, and allow users to interact with its content in a specific business context. It should be appreciated that content repositories may be separate logic sections in a same storage device.

The data and content management server 172 is typically a remote computer system accessible over a remote or local network, such as the network 150. The data and content management server 172 could be any commercially available computing devices. A client application (e.g., 121) process may be active on one or more user computing devices 120a-120n. The corresponding server process may be active on the data and content management server 172, as one of the front-end applications 113 described with reference to FIG. 2. The client application process and the corresponding server process may communicate with each other over the network 150, thus providing distributed functionality and allowing multiple client applications to take advantage of the information-gathering capabilities of the data and content management system 190.

In one implementation, the architecture 190 may be used for generating, aggregating and managing medical data, e.g., clinical trial data. A first data and content repository (e.g., 171a) may be used by a first sponsor (e.g., a pharmaceutical company) to store a first study design received from a first computing device (e.g., 120a). The first study design may define the infrastructure and lifecycle of the study, and may comprise rules (e.g., for queries, derived values, notifications and displaying events, forms and items), a casebook (i.e., a doctor's binder), event groups, events (e.g., patients visits), forms which comprise segregated sections and fields, item groups and items. In one example, a study design may define a particular study, i.e., each patient may have ten visits, and each visit may have three forms. There may be a workflow associated with each visit, e.g., what needs to be done at each visit.

In one implementation, the first study design may be stored as definition objects in the first data and content repository 171a, specifying what is required to happen on each site during the study. The first data and content repository 171a may also store electronic records of the first study. In one implementation, the electronic records may be Electronic Data Capture (EDC) data. Patient clinical trial source data may be captured at the user computing devices, and the aggregated and obfuscated data may be stored as EDC data in the first data and content repository 171a.

The second data and content repository 171b may be used by a first site (e.g., a hospital) of the first study to store clinical trial source data from a second user computing device (e.g., 120b), and a third data and content repository (e.g., 171c) may be used by a second site of the first study to store clinical trial source data from a third user computing device (e.g., 120c). The clinical trial source data (e.g., three blood pressure values of a patient taken during one visit) in the second data and content repository 171b may be converted to EDC data (e.g., the average of the three blood pressure values) automatically, and then stored in the first data and content repository 171a as EDC data. Similarly, the clinical trial source data in the third data and content repository 171c may be converted to EDC data automatically, and then stored in the first data and content repository 171a as EDC data. In one implementation, the clinical trial source data may be converted to the EDC data at the client application 121, and the EDC data is transmitted to the data and content management server 172. In one implementation, the clinical trial source data may be transmitted to the data and content repository 171b or 171c via the data and content management server 172, and converted to the EDC data at the data and content management server 172. The EDC data is then stored in the data and content repository 171a. Data in the second data and content repository 171b and the third data and content repository 171c may be synchronized with that in the first data and content repository 171a regularly or from time to time when new data entries are received from user computing devices. The first study design may be transmitted to the second data and content repository 171b and the third data and content repository 171c. The second repository and the third repository may be synchronized with the first repository for updates to the first study design.

In another implementation, data and content management server 172 may control the collection of the medical data, and also the operations and management of the clinical trial, including jobs or assignments to facilitate the real-time visibility and execution of the clinical trial. For instance, the clinical trial source data may be converted to the EDC data at the client application 121, and the EDC data is transmitted to data and content management server 172. In one implementation, the clinical trial source data may be transmitted to the data and content repository 171b or 171c via the data and content management server 172, and converted to the EDC data at the data and content management server 172.

The data and content management server 172 may receive the EDC data and then manage reimbursements to research sites and tracks the study budgets based on the received EDC data. The data and content management server 172 may also provide study management and monitoring capabilities. The data and content management server 172 may generate dashboards and reports tracking key indicators including enrollment and milestones based on the EDC data received from the data and content management server 172.

In another implementation, a first data and content repository (e.g., 171*a*) may be used by a sponsor (e.g., a pharmaceutical company) using a first computing device (e.g., 120*a*) to store EDC data received from a site (e.g., local lab) using a second computing device (e.g., 120*b*). The EDC data input by the second computing device may contain questionable content requiring verification. Queries may be created by the first computing device and managed by the medical data management server 172. The site (e.g., a local lab) may use the first repository (e.g. 171*a*) from a second user computing device (e.g., 120*b*) to answer the queries managed by the data and content management server 172. Upon satisfactory response, the query can be closed by the data and content management server 172. Alternatively, the first computing device (e.g., 120*a*) may create a subsequent query to be managed by the data and content management server 172.

In yet another implementation, a first repository (e.g., 171*a*) may be used by a first participant (e.g., a patient) using a first computing device (e.g., 120*a*) to store clinical outcome assessments. The clinical outcome assessments may collect data on patient reported outcomes, clinician reported outcomes, observer reported outcomes, and performance outcomes in clinical trials. A patient may input data about their symptoms, quality of life, or treatment experiences via questionnaires (e.g., pain scales, mood assessments). The first repository (e.g., 171*a*) may also be used by a second participant (e.g., a clinician) using a second computing device (e.g., 120*b*) to collect data on clinician reported outcomes. The clinician may record observations or assessments using standardized scales. The first repository (e.g., 171*a*) may also be used by a third participant (e.g., an observer) using a third computing device (e.g., 120*c*) to collect data on observer reported outcomes. The observer (e.g., caregiver or family members) may provide data on a patient's condition, especially when patients cannot report themselves (e.g., pediatric or cognitively impaired patients). The first repository (e.g., 171*a*) may also be used by a site using a fourth computing device (e.g., 120*d*) to collect data on performance outcomes in clinical trials. The site may objectively measure patient abilities, like physical or cognitive tasks, often captured through electronic tools.

The data and content management system may have a data duplication controller for data access management.

The data storage architecture 160 may be, e.g., a data warehouse, and may be operated by a third party.

Although the front-end applications 113, back-end systems 115, the data access controller 130 are shown in one server, it should be understood that they may be implemented in multiple computing devices.

In one implementation, the data and content management system 170 may be a multi-tenant system where various elements of hardware and software may be shared by one or more customers. For instance, a server may simultaneously process requests from a plurality of customers, and the data and content repositories 171 may store content for a plurality of customers. In a multi-tenant system, a user is typically associated with a particular customer. In one example, a user could be an employee of one of a number of pharmaceutical companies which are tenants, or customers, of the data and content management system 170.

In one embodiment, the data and content management system 170 may run on a cloud computing platform. Users can access content on the cloud independently by using a virtual machine image, or purchasing access to a service maintained by a cloud database provider.

In one embodiment, the data and content management system 170 may be provided as Software as a Service ("SaaS") to allow users to access the data and content management system 170 with a thin client.

Figure 2:
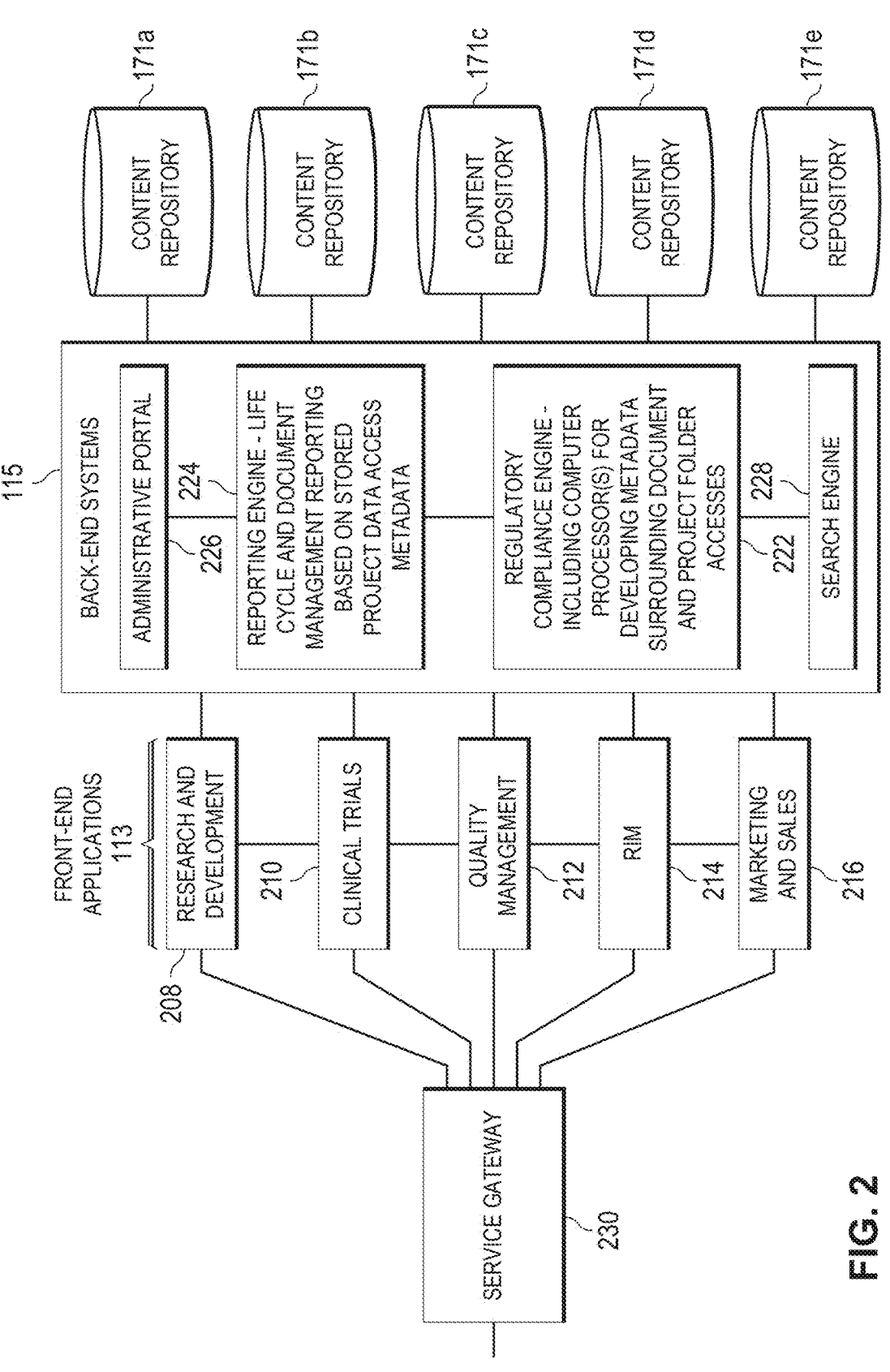
FIG. 2 provides a description of the content management system with additional specific applications and interfaces connected thereto.

FIG. 2 provides a description of the data and content management system 170 with additional specific applications and interfaces connected thereto. In an embodiment, this data and content management system 170 is a cloud-based or distributed network based system for consolidating an enterprise's data, oftentimes integrating multiple content repositories in an enterprise into a single system having coordinated control, measuring, and auditing of data creation, access and distribution.

In an embodiment of the data and content management system 170 for the life sciences industry, as illustrated in the figure, this data and content management system 170 can include specific data collections for the following areas and/or business process-specific front-end applications 113:

A Research & Development (R&D) front-end application 208 provides for an aggregation of materials in support of research and initial clinical trial submissions through building organized and controlled content repositories within the data and content management system 170, more specifically, the content repository 171*a*. Elements that can be stored, organized, and managed through this front-end include submission bills of materials, Drug Information Association (DIA) reference models support, and submission-ready renderings. This front-end 208 is designed to provide an interface to the data and content management system 170 whereby researchers, contract research organizations (CROs), and other collaboration partners can access and/or distribute content through a single controlled document system.

A clinical trials front-end application 210 provides for faster and more organized access to trial documents and reports, while supporting seamless collaboration between sponsors, CROs, sites, investigators and other trial participants. Specific features both ease study and site administration as well as support the DIA trial master file (TMF) reference model. Having this front-end application providing access to the data and content management system 170 further provides for efficient passing off of content, e.g., in the content repository 171*b*, between this phase and other phases of the life sciences development process.

A manufacturing and quality application 212 enables the creation, review, approval and distribution of controlled documents across the organization and with external partners in the context of materials control and other manufacturing elements. The application 212 provides functionality in support of the manufacturing process including watermarking, controlled print, signature manifestation and "Read and Understood" signature capabilities. The documents and metadata associated with this process is managed and stored in the data and content management system 170, or more specifically, the content repository 171*c*, whereby it can be assured that the related documents are not distributed in contravention of law and company policy. The application 212 also manages business processes including change control, complaints, corrective actions and preventive actions ("CAPA"), deviation and audits.

A regulatory information management ("RIM") application 214 provides for management of regulatory information, submission processes and submission reports, which may include, e.g., safety reporting, product registrations, health authority interactions, central and local requirements, submissions to health authorities, and health authority information management. The product registration information may include, e.g., the associated product information, application information, application date, registration details, key registration dates, marketing status, and marketing details. The health authority interactions may include bidirectional interactions with health authorities globally, including correspondences, commitments and queries. Pharmaceutical companies may submit registration applications to health authorities to get approval for selling products in a country. The registration process may take a few months and status of the registration may change over time. User may see global registrations and their status in one or more submission reports. Related documents may be stored in the content repository 171d.

A marketing and sales application 216 provides an end-to-end solution for the development, approval, distribution, expiration and withdrawal of promotional materials. Specific features include support for global pieces, approved Form FDA (Food and Drug Administration) 2253 (or similar international forms) form generation, online document, and video annotation, and a built-in digital asset library (DAL). Again, the communications may be through the data and content management system 170, and the promotional materials may be stored in the content repository 171e.

The data and content management system 170 may have a number of back-end system applications 115 that provide for the management of the data, forms, and other communications in. For example, the back-end systems applications 115 may include a regulatory compliance engine 222 to facilitate regulatory compliance, including audit trail systems, electronic signatures systems, and system traceability to comply with government regulations, such as 21 CFR Part 11, Annex 11 and GxP-related requirements. The regulatory compliance engine 222 may include processors for developing metadata surrounding document and project folder accesses so from a regulatory compliance standpoint it can be assured that only allowed accesses have been permitted. The regulatory compliance engine 222 may further includes prevalidation functionality to build controlled content in support of installation qualification (IQ) and/or operational qualification (OQ), resulting in significant savings to customers for their system validation costs.

The back-end systems 115 may contain a reporting engine 224 that reports on documents, their properties and the complete audit trail of changes. These simple-to-navigate reports show end users and management how content moves through its life cycle over time, enabling the ability to track 'plan versus actual' and identify process bottlenecks. The reporting engine may include processors for developing and reporting life cycle and document management reporting based on stored project data and access metadata relative to documents, forms and other communications stored in the data and content management system 170.

The back-end systems 115 can include an administrative portal 226 whereby administrators can control documents, properties, users, security, workflow and reporting with a simple, point-and-click web interface. Customers also have the ability to quickly change and extend the applications or create brand new applications, including without writing additional software code.

The back-end systems 115 may include a search engine 228 whereby the data and content management system 170 can deliver simple, relevant and secure searching.

The data and content management system 170 may have more back-end systems.

In providing this holistic combination of front-end applications 113 and back-end systems 115, the various applications can further be coordinated and communicated with by the service gateway 230, which in turn can provide for communications with various web servers and/or web services APIs. Such web servers and/or web services APIs can include access to the content and metadata layers of some or all of the various front-end applications 113 and back end systems 115, enabling seamless integration among complementary systems.

In the context of the described embodiments, updates in one repository, e.g., the content repository 171c for the quality management application front-end application 212, may be shared with a repository (e.g., the RIM repository 171d) for another front-end application (e.g., the RIM application 214).

The data and content management system 170 may store content for other industries.

Figure 3:
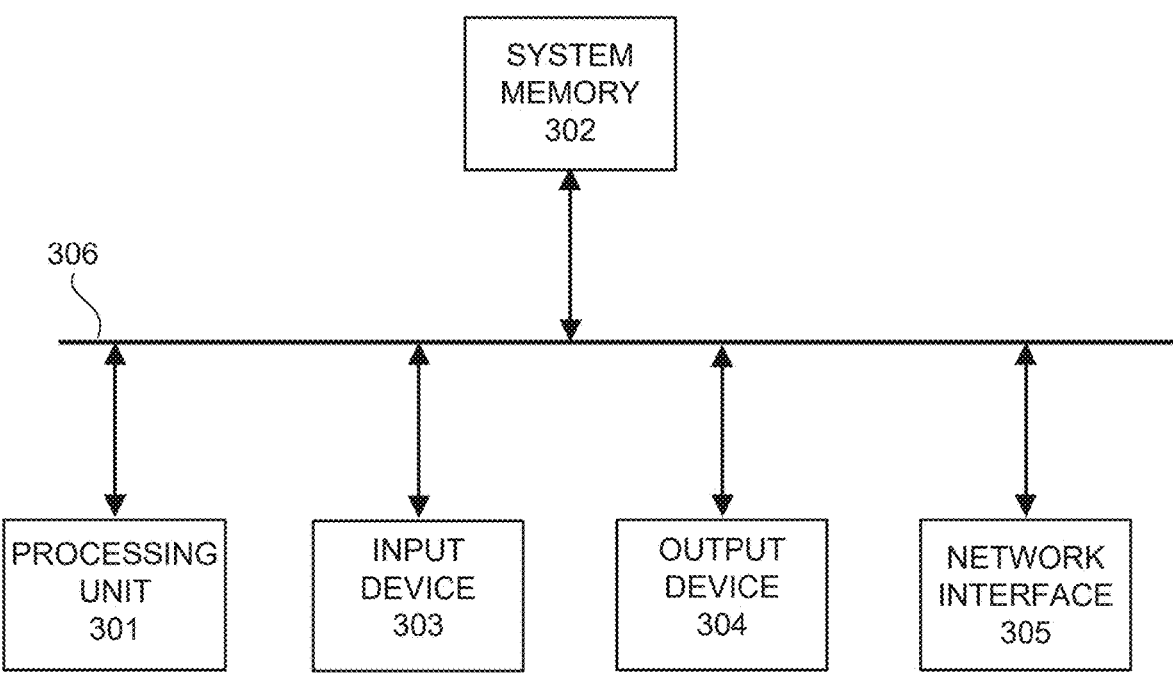
FIG. 3 illustrates an example block diagram of a computing device.

FIG. 3 illustrates an example block diagram of a computing device 300 which can be used as the user computing devices 120a-120n, and the data management server 112 and data and content management server 172 in FIG. 1. The computing device 300 is only one example of a suitable computing environment and is not intended to suggest any limitation as to scope of use or functionality. The computing device 300 may include a processing unit 301, a system memory 302, an input device 303, an output device 304, a network interface 305 and a system bus 306 that couples these components to each other.

The processing unit 301 may be configured to execute computer instructions that are stored in a computer-readable medium, for example, the system memory 302. The processing unit 301 may be a central processing unit (CPU).

The system memory 302 typically includes a variety of computer readable media which may be any available media accessible by the processing unit 301. For instance, the system memory 302 may include computer storage media in the form of volatile and/or nonvolatile memory such as read only memory (ROM) and/or random access memory (RAM). By way of example, but not limitation, the system memory 302 may store instructions and data, e.g., an operating system, program modules, various application programs, and program data.

A user can enter commands and information to the computing device 300 through the input device 303. The input device 303 may be, e.g., a keyboard, a touchscreen input device, a touch pad, a mouse, a microphone, and/or a pen.

The computing device 300 may provide its output via the output device 304 which may be, e.g., a monitor or other type of display device, a speaker, or a printer.

The computing device 300, through the network interface 305, may operate in a networked or distributed environment using logical connections to one or more other computing devices, which may be a personal computer, a server, a router, a network PC, a peer device, a smart phone, or any other media consumption or transmission device, and may include any or all of the elements described above. The logical connections may include a network (e.g., the network 150) and/or buses. The network interface 305 may be configured to allow the computing device 300 to transmit and receive data in a network, for example, the network 150. The network interface 305 may include one or more network interface cards (NICs).

Figure 4:
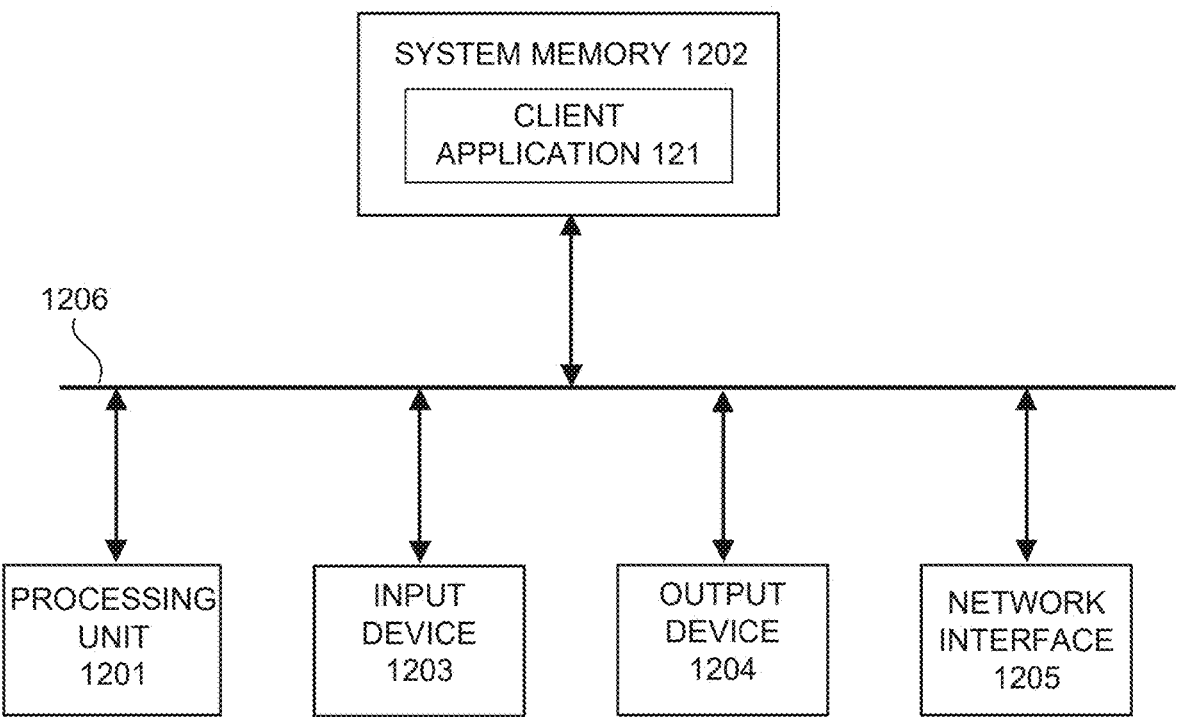
FIG. 4 illustrates an example high level block diagram of a user computing device.

FIG. 4 illustrates an example high level block diagram of a user computing device (e.g., 120a) wherein the present invention may be implemented. The user computing device 120a may be implemented by the computing device 300 described above, and may have a processing unit 1201, a system memory 1202, an input device 1203, an output device 1204, and a network interface 1205, coupled to each other via a system bus 1206. The system memory 1202 may store the client application 121.

Figure 5:
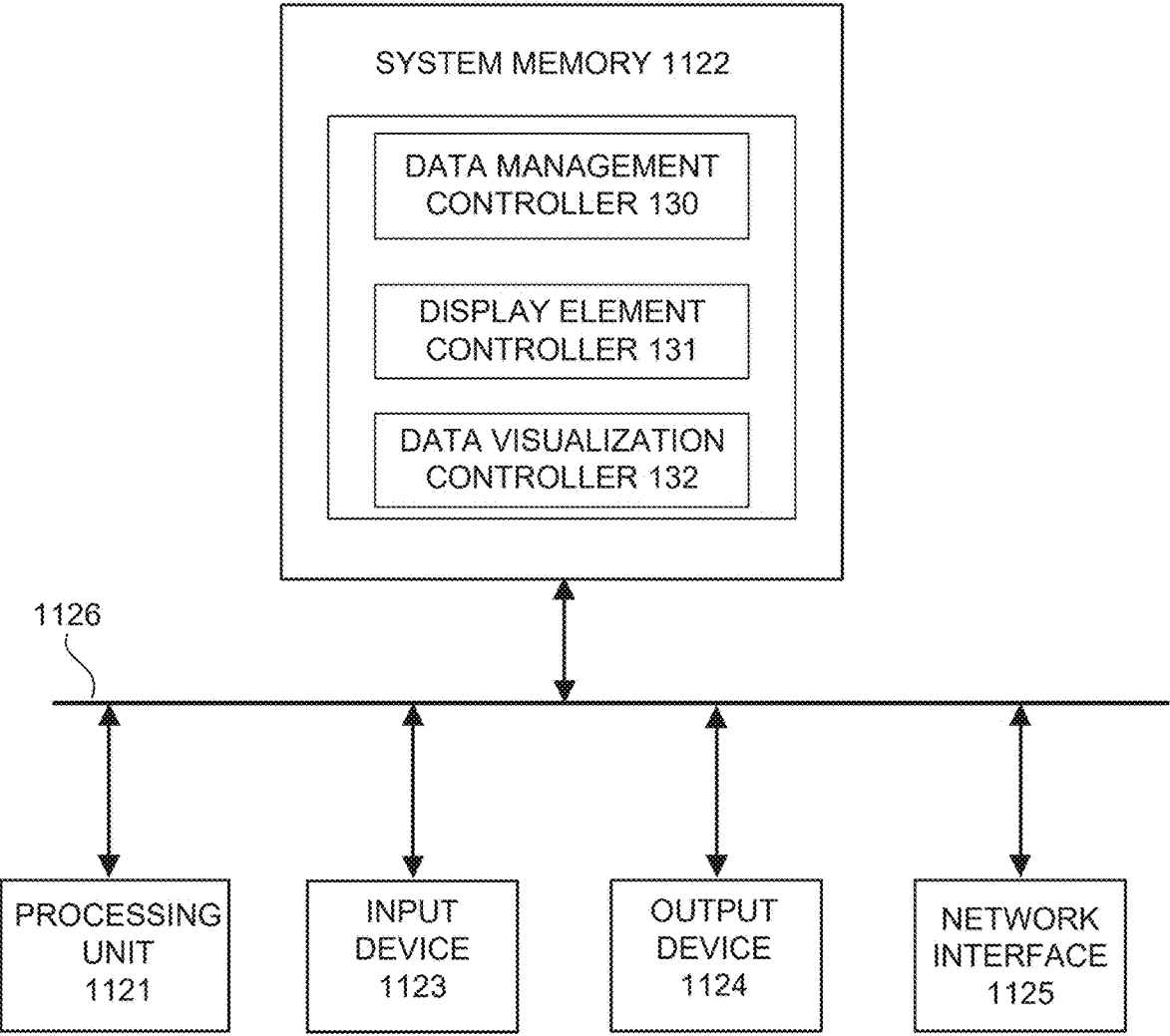
FIG. 5 illustrates an example high level block diagram of the data management server according to one embodiment of the present invention.

FIG. 5 illustrates an example high level block diagram of the data management server 112 according to one embodiment of the present invention. The data management server 112 may be implemented by the computing device 300, and may have a processing unit 1121, a system memory 1122, an input device 1123, an output device 1124, and a network interface 1125, coupled to each other via a system bus 1126. The system memory 1122 may store the data management controller 130, display element controller 131, and data visualization controller 132.

In an example implementation, a first repository (e.g., 171a) may be used by a first participant (e.g., a patient) using a first computing device (e.g., 120a) to store clinical outcome assessments. The clinical outcome assessments may collect data on patient reported outcomes, clinician reported outcomes, observer reported outcomes, and performance outcomes in clinical trials. A patient may input data about their symptoms, quality of life, or treatment experiences via questionnaires (e.g., pain scales, mood assessments). The first repository (e.g., 171a) may also be used by a second participant (e.g., a clinician) using a second computing device (e.g., 120b) to collect data on clinician reported outcomes. The clinician may record observations or assessments using standardized scales. The first repository (e.g., 171a) may also be used by a third participant (e.g., an observer) using a third computing device (e.g., 120c) to collect data on observer reported outcomes. The observer (e.g., caregiver or family members) may provide data on a patient's condition, especially when patients cannot report themselves (e.g., pediatric or cognitively impaired patients). The first repository (e.g., 171a) may also be used by a site using a fourth computing device (e.g., 120d) to collect data on performance outcomes in clinical trials. The site may objectively measure patient abilities, like physical or cognitive tasks, often captured through electronic tools.

Figure 6:
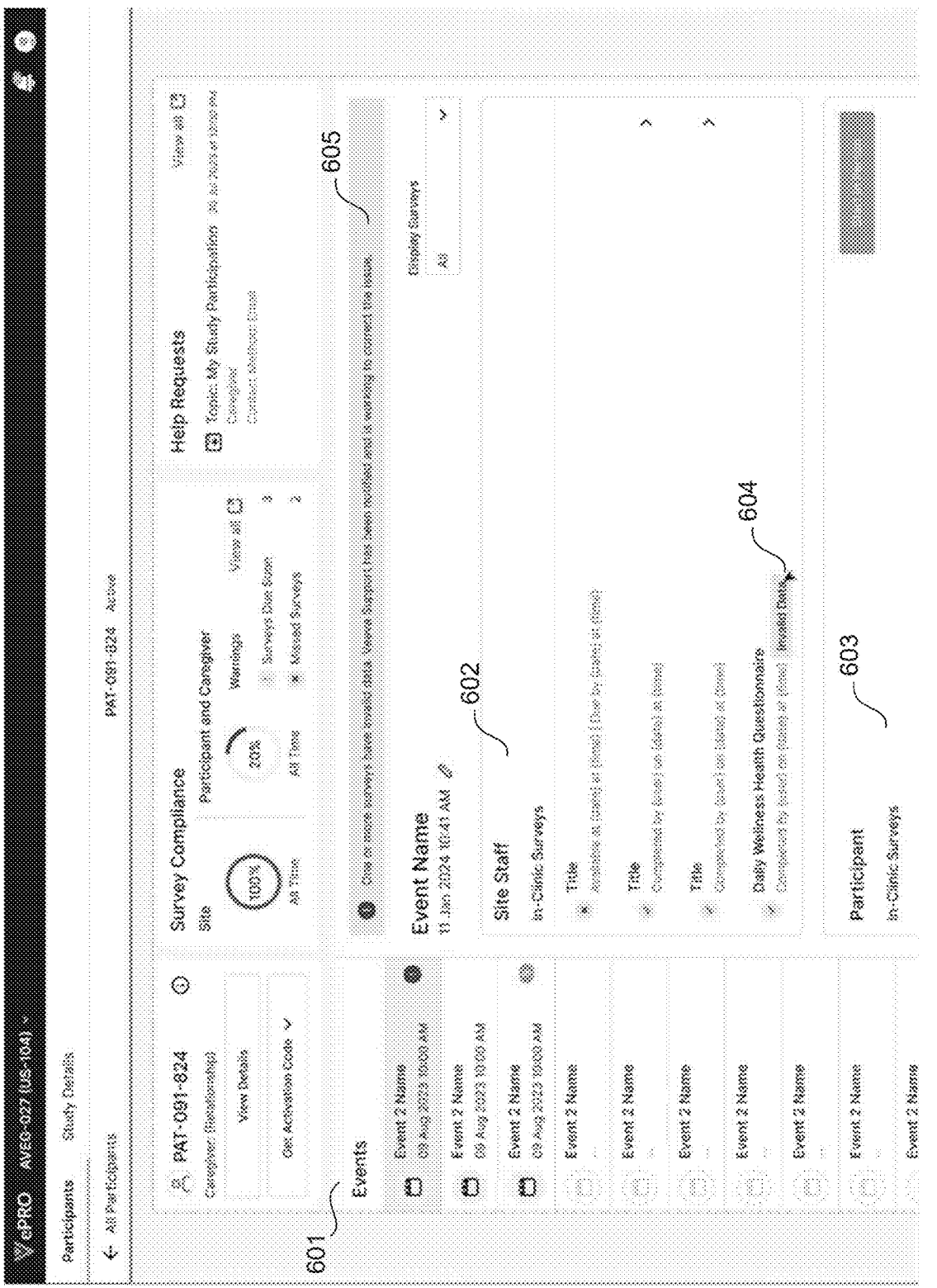
FIG. 6 illustrates an example user interface for quarantine preservation of data integrity in data management systems according to one embodiment of the present invention.

Referring now to FIG. 6, an example user interface 600 for quarantine preservation of data integrity in data management systems is shown. As depicted, a listing of events (e.g., patient visits) is shown in the left pane 601. Each event may have one or more outcome assessments associated. For example, a clinician reported outcome assessment (e.g., by the site staff) may be collected and managed at 602. Similarly, a clinical outcome assessment (e.g., by the patient) may be collected and managed at 603. When an outcome assessment is submitted using the user interface 600, a first set of validation checks may be performed by the user computing device (e.g., 120a). The first set of validation checks may be a series of client side validation checks, including but not limited to checking for required fields, checking for format, and/or checking for valid data types. Each outcome assessment may be individually configured with multiple separate required fields, formats, or valid data types within the document. An outcome assessment that fails the first series of client side validation checks will reject the outcome assessment submission in the user interface 600. An error notification will be displayed to the user to indicate the failed validation and a suggestion for correction. When the user computing device (e.g., 120a) executes the first set of validation checks successfully, the outcome assessment is forwarded to the data and content management server 172 for processing. The data and content management controller 130 executes a second set of validation checks. The second set of validation checks may be a series of server-side validations performed on the backend including, but not limited to uniqueness constraints, complex business rules, cross-referencing with other database records, consistency checks. As depicted in FIG. 6, an invalid data error failing complex business logic is detected with a notification 604. The clinician reported outcome assessment 602 had a date that was outside the bounds of acceptance. It may be the case that the clinician reported outcome assessment 602 was available from a given start datetime, and due by a given end datetime. The submitted datetime was not within the given start and end datetime, which triggered an error. When the second set of validation checks is successfully verified, there will be an absence of error notifications (e.g., 604, 605) with valid check notifications to indicate success. The data and content management controller 130 proceeds to store the submitted outcome assessments to a corresponding repository (e.g., 171a).

When there is an error in any of the secondary validation checks in the series of server-side validation checks, the data and content management controller 130 stores the submitted outcome assessments in a staging database, or quarantine repository (e.g., 171b). The data and content management server 172 accepts and persists the data regardless of whether the second set of validation checks are successful. This ensures the data is captured and moved off the client device immediately. The submitted outcome assessments with failed validations are not written to the production database (e.g., 171a). Since the data is stored on the server side from the moment of initial receipt, the risk of data loss due to client application uninstallation, data clearing, or device failure is eliminated. The data is retained until it is either successfully corrected or explicitly purged by an administrator.

The data and content management controller 130 transitions and records the submitted outcome assessment into a quarantine state. The error is recorded in the audit logs with details including but not limited to the participant (e.g., internal ID of study participant, external participant name of the study participant), respondent (e.g., internal/external participant, caregiver, or site staff, respondent type), survey (e.g., internal ID of user survey, external display name of survey), study (e.g., internal ID of sponsor study, external global study ID of sponsor study), site (e.g., internal study ID of site, external global study site ID of site), due date, survey submission date (e.g., completed at, and completed on).

Once corrections are made to address the errors identified in the second set of validation checks, a new outcome assessment may be uploaded. In one implementation, a CSV file containing the corrected patient response date may be uploaded. Once the corrections are received, the quarantine correction process is started.

In one implementation, the new outcome assessment adjusted to correct the previously detected errors may be resubmitted using the user interface 600. The first set of validation checks may be performed by the user computing device (e.g., 120a) again, and the data and content management controller 130 executes the second set of validation checks again. In another implementation, the modified outcome assessment may only undergo a second attempt at backend validation while foregoing the first set of validation checks to save processing time.

When the second attempt at backend validation completes with no errors, the data and content management controller 130 updates to remove the quarantine status and proceeds to store the updated outcome assessment to the corresponding production repository (e.g., 171*a*) for access.

In one implementation, quarantined data may be accepted but not validated data and may be treated from the participant perspective as if they are completed and validated. This ensures for compliance purposes quarantined surveys shall be counted as compliant and not missed. The submission datetime may remain the original submission datetime for compliance calculation purposes.

In another implementation, outcome assessments that pass client side validation and submitted to the data and content management server 172, will be accepted onto the server regardless of passing back-end validation. The survey may be stored in the data architecture 160.

In one implementation, a CSV data file may be generated containing one record per DCR containing columns: jira (string), user_survey_id (uuid), question id (string), current_answer (string), new answer (string), and reason (string). This CSV data file may then be uploaded to a new path in the data architecture 160. Correction is written to the data management system and an audit trail is generated.

While various embodiments have been described above, it should be understood that they have been presented by way of example only, and not limitation. Thus, the breadth and scope of a preferred embodiment should not be limited by any of the above described exemplary embodiments, but should be defined only in accordance with the claims and their equivalents for any patent that issues claiming priority from the present provisional patent application.

In all descriptions of "servers" or other computing devices herein, whether or not the illustrations of those servers or other computing devices similarly show a server-like illustration in the figures, it should be understood that any such described servers or computing devices will similarly per form their described functions in accordance with computer readable instructions stored on a computer-readable media that are connected thereto.

Resources may encompass any types of resources for running instances including hardware (such as servers, clients, mainframe computers, networks, network storage, data sources, memory, central processing unit time, Scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and Software infrastructures configured to form a virtual organization comprised of multiple resources which may be in geographically disperse locations.

Various terms used herein have special meanings within the present technical field. Whether a particular term should be construed as such a "term of art, depends on the context in which that term is used. "Connected to," "in communication with or other similar terms should generally be construed broadly to include situations both where communications and connections are direct between referenced elements or through one or more intermediaries between the referenced elements, including through the Internet or some other communicating network. "Network," "system," "environment," and other similar terms generally refer to networked computing systems that embody one or more aspects of the present disclosure. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

The steps and/or operations described above in relation to an embodiment of the present disclosure may occur in a different order, or in parallel, or concurrently for different epochs, etc. depending on the specific embodiment and/or implementation, as would be understood by one of ordinary skill in the art. Different embodiments may perform actions in a different order or by different ways or means. As would be understood by one of ordinary skill in the art, some drawings are simplified representations of the actions performed, their descriptions herein simplified overviews, and real-world implementations would be much more complex, require more stages and/or components, and would also vary depending on the requirements of the particular implementation. Being simplified representations, these drawings do not show other required steps as these may be known and understood by one of ordinary skill in the art and may not be pertinent and/or helpful to the present description.

Similarly, some drawings are simplified block diagrams showing only pertinent components, and some of these components merely represent a function and/or operation well-known in the field, rather than an actual piece of hardware, as would be understood by one of ordinary skill in the art. In such cases, some or all of the components/modules may be implemented or provided in a variety and/or combinations of manners, such as at least partially firmware and/or hardware, including, but not limited to one or more application-specific integrated circuits ("ASICS"), standard integrated circuits, controllers executing appropriate instructions, and including microcontrollers and/or embedded controllers, field-programmable gate arrays ("FPGAs"), complex programmable logic devices ("CPLDs"), and the like. Some or all of the system components and/or data structures may also be stored as contents (e.g., as executable or other machine-readable software instructions or structured data) on a non-transitory computer-readable medium (e.g., as a hard disk; a memory; a computer network or cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use or provide the contents to perform at least some of the described techniques.

One or more processors, simple micro controllers, controllers, and the like, whether alone or in a multi-processing arrangement, may be employed to execute sequences of instructions stored on non-transitory computer-readable media to implement embodiments of the present disclosure. In some embodiments, hard-wired circuitry may be used in place of or in combination with software instructions. Thus, embodiments of the present disclosure are not limited to any specific combination of hardware circuitry, firmware, and/or software.

The term "computer-readable medium" as used herein refers to any medium that stores instructions which may be provided to a processor for execution. Such a medium may take many forms, including but not limited to, non-volatile and volatile media. Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, or any other medium on which instructions which can be executed by a processor are stored.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field, such claims should not be limited by the language chosen under this heading to describe the so-called technical field. Further, a description of a technology in the "Background is not to be construed as an admission that technology is prior art to any invention(s) in this disclosure. Neither is the "Brief Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The invention claimed is:

1. A computer-implemented method for quarantine preservation of outcome assessment data integrity in data management systems, the computer-implemented method comprising:

receiving, by the data management system, an outcome assessment collecting data on patient reported outcomes that successfully complete a first set of client-side validations, wherein the first set of client-side validations include a series of validations checking for required fields and format checks;

executing, by the data management system, a second set of server-side validations including a series of validations checking for uniqueness constraints, complex business rules, cross-referencing with other database records, and consistency;

when one server-side validation in the second set of server-side validations fails, storing the outcome assessment successfully completing the first set of client side validations in a quarantine repository;

updating the outcome assessment status to quarantined state;

modifying, by the data management system, the outcome assessment to correct the failed server-side validation;

16 subsequently executing, by the data management system, the second set of server-side validations a second time; and when the second set of server-side validations completes with no errors, updating the outcome assessment status and storing the modified outcome assessment.

2. The computer-implemented method of claim 1 above, wherein the patient reported outcomes include symptoms, quality of life, or treatment experiences via questionnaires, pain scales, or mood assessments.

3. The computer-implemented method of claim 1 above, wherein the outcome assessment collects data on clinician reported outcomes.

4. The computer-implemented method of claim 3, above, wherein the clinician reported outcomes include observations or assessments using standardized scales.

5. The computer-implemented method of claim 1 above, wherein the outcome assessment collects data on observer reported outcomes, wherein the observer includes caregivers or family members of a patient.

6. The computer-implemented method of claim 5, above, wherein the observer reported outcome includes data on the patient's condition when the patient cannot report themselves because of impairment.

7. The computer-implemented method of claim 1 above, wherein the outcome assessment collects data on performance outcomes in clinical trials.

8. The computer implemented method of claim 7, above, wherein the performance outcomes in the clinical trials include patient abilities, physical tasks, and cognitive tasks measured using electronic tools.

9. The computer-implemented method of claim 1 above, further comprising:

receiving, by the data management system, a second outcome assessment successfully completing the first set of client-side validations, wherein the first set of client-side validations include a series of validations checking for required fields and format checks;

executing, by the data management system, the second set of server-side validations including a series of validations checking for uniqueness constraints, complex business rules, cross-referencing with other database records, and consistency;

when one server-side validation in the second set of server-side validations fails, storing the second outcome assessment successfully completing the first set of client side validations in a quarantine repository;

updating the second outcome assessment status to quarantined state;

modifying, by the data management system, the second outcome assessment to correct the failed server-side validation;

subsequently executing, by the data management system, the second set of server-side validations for the second outcome assessment a second time; and when the second set of server-side validations completes with no errors, updating the second outcome assessment status and storing the modified outcome assessment.

10. A data management system for quarantine preservation of outcome assessment data integrity, the data management system comprising:

a quarantine repository for storing one or more outcome assessments;

a production repository for storing one or more outcome assessments;

a network interface configured to facilitate data communication via a network; and a processing circuit comprising a processor and a memory, the processing circuit configured to:

receiving an outcome assessment collecting data on patient reported outcomes that successfully completes a first set of client-side validations, wherein the first set of client-side validations include a series of validations checking for required fields and format checks;

executing a second set of server-side validations including a series of validations checking for uniqueness constraints, complex business rules, cross-referencing with other database records, and consistency;

when one server-side validation in the second set of server-side validations fails, storing the outcome assessment successfully completing the first set of client side validations in the quarantine repository;

updating the outcome assessment status to quarantined state;

modifying the outcome assessment to correct the failed server-side validation;

subsequently executing the second set of server-side validations a second time; and when the second set of server-side validations completes with no errors, updating the outcome assessment status and storing the modified outcome assessment.

11. A non-transitory computer-readable medium including instructions that, when executed by one or more processors, cause the one or more processors to perform the steps of:

receiving an outcome assessment collecting data on patient reported outcomes that successfully completes first set of client-side validations, wherein the first set of client-side validations include a series of validations checking for required fields and format checks;

executing a second set of server-side validations including a series of validations checking for uniqueness constraints, complex business rules, cross-referencing with other database records, and consistency;

when one server-side validation in the second set of server-side validations fails, storing the outcome assessment successfully completing the first set of client side validations in a quarantine repository;

updating the outcome assessment status to quarantined state;

modifying the outcome assessment to correct the failed server-side validation;

subsequently executing the second set of server-side validations a second time; and when the second set of server-side validations completes with no errors, updating the outcome assessment status and storing the modified outcome assessment.

* * * * *